(12) United States Patent
Cunningham

(10) Patent No.: US 6,199,022 B1
(45) Date of Patent: Mar. 6, 2001

(54) DRIVE CIRCUIT MODAL FILTER FOR A VIBRATING TUBE FLOWMETER

(75) Inventor: Timothy J. Cunningham, Boulder, CO (US)

(73) Assignee: Micro Motion, Inc., Boulder, CO (US)

( * ) Notice: Subject to any disclaimer, the term of this patent is extended or adjusted under 35 U.S.C. 154(b) by 0 days.

(21) Appl. No.: 08/890,785

(22) Filed: Jul. 11, 1997

(51) Int. Cl.$^7$ ........................................... G01F 1/58

(52) U.S. Cl. ..................... 702/54; 702/45; 702/194; 73/861.356; 73/861.355; 73/861.354

(58) Field of Search ........................ 702/33, 36, 39, 702/41, 45, 48, 50, 54, 56, 77, 100, 103, 106, 113, 114, 124, 126, 142, 150, 189, 190, 191, 194, 196, 197, 198, 199, FOR 123, FOR 126, FOR 128, FOR 124, FOR 172, FOR 150, FOR 164, FOR 166, FOR 170; 700/281, 282, 280, 275, 279; 73/861.354–861.357, 32 A, 1.16, 1.35, 1.82, 578, 570, 579, 668, 662–665, 152.32, 861.02, 861.03, 861.18, 861.19, 861.23, 861.24

(56) References Cited

U.S. PATENT DOCUMENTS

| | | | |
|---|---|---|---|
| 4,777,833 | 10/1988 | Carpenter | 73/861.38 |
| 4,781,069 | 11/1988 | Mitzner | 73/861.38 |
| 5,009,109 | 4/1991 | Kalotay et al. | 73/861.38 |
| 5,301,557 | 4/1994 | Cage et al. | 73/861.38 |
| 5,469,748 | * 11/1995 | Kalotay | 73/861.356 |
| 5,555,190 | * 9/1996 | Derby et al. | 702/106 |
| 5,734,112 | 3/1998 | Bose et al. | 73/861.56 |
| 5,827,979 | * 10/1998 | Schottet et al. | 73/861.357 |

FOREIGN PATENT DOCUMENTS

| | | | |
|---|---|---|---|
| 4413239A1 | 5/1995 | (DE) | G01F/1/84 |
| 0 578 113 A2 | 12/1984 | (EP) | G01F/1/84 |
| 0462711A1 | 5/1991 | (EP) | G01F/1/84 |
| 0 701 107 A2 | 3/1996 | (EP) | G01F/1/00 |
| WO 92/14123 | 8/1992 | (WO) | G01F/1/84 |
| WO 95/16897 | 6/1995 | (WO) | G01F/1/84 |
| WO 95/29385 | 11/1995 | (WO) | G01F/1/84 |
| WO 97/40348 | 10/1997 | (WO) | G01F/1/84 |
| WO 98/07009 | 2/1998 | (WO) | G01F/1/84 |

OTHER PUBLICATIONS

Thesis on "Modal Analysis and Zero Stability of Coriolis Mass Flowmeters" by Timothy J. Cunningham; Colorado State University, Fall 1993, p. ii–vii,1–92. (No month).

"Application of Modal Filtering Techniques to Vibration Control of a Precision Truss" by Albert Bosse and Shalom Fisher; AD—vol. 45/MD—vol. 54 Adaptive Structures and Composite Materials: Analysis and Application 1994; pp. 281–285. (No month).

(List continued on next page.)

* cited by examiner

Primary Examiner—Hal Wachsman
(74) Attorney, Agent, or Firm—Duft, Graziano & Forest, P.C.

(57) ABSTRACT

A drive system for a vibrating tube-based measurement instrument employing a spatial filter to produce a drive signal having modal content only at a desired vibration mode. Multiple feedback sensors located at different locations along a vibrating tube produce multiple feedback sensors. Each feedback signal has applied to it a weighting or gain factor. All of the weighted feedback signals are then summed to produce a drive signal, or a signal proportional to a drive signal, having improved modal content as compared to any of the feedback signals by themselves. The weighting factors are selected by any of several means. One method is to build the eigenvector matrix for the vibrating flow tube by extracting the eigenvectors from a finite element model of the vibrating structure. The inverse or psuedo-inverse of the eigenvector matrix is calculated to obtain the modal filter vector. The appropriate set of weighting coefficients are selected from the modal filter vector.

30 Claims, 9 Drawing Sheets

OTHER PUBLICATIONS

"A New Type of Single Straight Tube Coriolis Mass Flowmeter" by A. Rieder and Dr. W. Drahm; pp. 250–255, (No date).

"Zero Shifts in Coriolos Sensors Due to Imbalance" by T.J. Cunningham; 1994; pp. 1–10. (No month).

Adiletta G et al: "A Twin Rigid Straight Pipe Coriolis Mass Flowmeter" Measurement, vol. 11, No. 41 Jul. 1993, Amsterdam, NL, pp. 289–308, XP000387399.

Cunningham; "Zero Shift Due To Non–Proportional Damping", Micro Motion Report #10233, Part of IMAC XV, Feb. 1997, Session 8j, Structural Damping, pp. 1–7.

Bosse et al.; "Application Of Modal Filtering Techinques To Vibration Control Of Precision Truss", AD–vol.45/MD–vol. 54, Adaptive Structures and Composite Material, Analysis and Application ASME 1994, pp. 281–285. (No month).

Cunningham; "Zero Shifts In Coriolis Sensors Due To Imbalance", Procedings of AIAA/ASME/AHS/ASC $35^{35}$, Structures, Structural Dynamics and Materials Conference, Apr. 18–20, 1994, AIAA Paper 94–1621 (A94–2411a).

Stack, Garnett, Pawlas; "A Finite Element For The Vibration Analysis Of Fluid–Conveying Timoshenko Beam", AIAA Paper 93–1552, pp. 1–10 (1993). (No month).

Timothy J. Cunningham, Modal Analysis and Zero Stability of Coriolis Mass Flowmeters (1993) (M. of Science Thesis, Colorado State University (Fort Collins)). (No month).

DRIVE CIRCUIT MODAL FILTER FOR A VIBRATING TUBE FLOWMETER

FIELD OF THE INVENTION

The present invention relates to apparatus and methods of generating a drive signal for a Coriolis mass flowmeter driver. More particularly the present invention relates to generating a drive signal which excites only the desired vibration mode in the vibrating flow tube of the Coriolis flowmeter. More particularly the present invention relates to using modal filters to suppress the undesirable drive signal components and enhance the desirable drive signal components.

STATEMENT OF THE PROBLEM

It is known to use Coriolis effect mass flowmeters to measure mass flow and other information for materials flowing through a conduit. Exemplary Coriolis flowmeters are disclosed in U.S. Pat. Nos. 4,109,524 of Aug. 29, 1978, 4,491,025 of Jan. 1, 1985, and Re. 31,450 of Feb. 11, 1982, all to J. E. Smith et al. These flowmeters have one or more flow tubes of straight or curved configuration. Each flow tube configuration in a Coriolis mass flowmeter has a set of natural vibration modes, which may be of a simple bending, torsional or coupled type. Each flow tube is driven to oscillate at resonance in one of these natural modes. Material flows into the flowmeter from a connected conduit on the inlet side of the flowmeter, is directed through the flow tube or tubes, and exits the flowmeter through the outlet side. The natural vibration modes of the vibrating, material filled system are defined in part by the combined mass of the flow tubes and the material flowing within the flow tubes.

When there is no flow through the flowmeter, all points along the flow tube oscillate due to an applied driver force with identical phase or small initial fixed phase offset which can be corrected. As material begins to flow, Coriolis forces cause each point along the flow tube to have a different phase. The phase on the inlet side of the flow tube lags the driver, while the phase on the outlet side leads the driver. Pick-off sensors are placed on the flow tube to produce sinusoidal signals representative of the motion of the flow tube. Signals output from the pick-off sensors are processed to determine the phase difference between the pick-off sensors. The phase difference between two pick-off sensor signals is proportional to the mass flow rate of material through the flow tube.

An essential component of every Coriolis flowmeter, and of every vibrating tube densitometer, is the drive or excitation system. The drive system operates to apply a periodic physical force to the flow tube which causes the flow tube to oscillate. The drive system includes a driver mounted to the flow tube(s) of the flowmeter. The driver mechanism typically contains one of many well known arrangements, such as a magnet mounted to one conduit and a wire coil mounted to the other conduit in an opposing relationship to the magnet. A drive circuit continuously applies a periodic, typically sinusoidally or square shaped, drive voltage to the driver. Through interaction of the continuous alternating magnetic field produced by the coil in response to the periodic drive signal and the constant magnetic field produced by the magnet, both flow conduits are initially forced to vibrate in an opposing sinusoidal pattern which is thereafter maintained. Those skilled in the art recognize that any device capable of converting an electrical signal to mechanical force is suitable for application as a driver. (See U.S. Pat. No. 4,777,833 issued to Carpenter and assigned on its face to Micro Motion, Inc.) Also, one need not use a sinusoidal signal but rather any periodic signal may be appropriate as the driver signal (see U.S. Pat. No. 5,009,109 issued to Kalotay et. al. and assigned on its face to Micro Motion, Inc.).

A typical mode, although not the only mode, in which Coriolis flowmeters are driven to vibrate is the first out-of-phase bending mode. The first out-of-phase bending mode is the fundamental bending mode at which the two tubes of a dual tube Coriolis flowmeter vibrate in opposition to one another. However, this is not the only mode of vibration present in the vibrating structure of a Coriolis flowmeter driven in the first out-of-phase bending mode. There are, of course, higher modes of vibration which may be excited. There is also, as a result of fluid flowing through the vibrating flow tube and the consequent Coriolis forces, a first out-of-phase twist mode that is excited as well as other modes. There are also in-phase and lateral modes of vibration. Ultimately, there are hundreds of vibration modes actually excited in a Coriolis flowmeter that is driven to oscillate in the first out-of-phase bending mode. Even within relatively narrow range of frequencies near the first out-of-phase bending mode there are at least several additional modes of vibration. In addition to multiple modes being excited by the driven excitation of the flow tubes, modes can be excited due to vibrations external to the flowmeter. For example, a pump located elsewhere in a process line might generate a vibration along a pipeline that excites a mode of vibration in a Coriolis flowmeter. Another reason that additional and undesirable modes are sometimes excited in a Coriolis flowmeter is when manufacturing tolerances are such that the driver elements are not located symmetrically on the flow tubes. This results in the driver putting eccentric forces into the flow tubes hence exciting multiple modes of vibration. Thus a Coriolis flowmeter driven to oscillate or resonate at the first out-of-phase bending mode actually has a conduit(s) oscillating in many other modes in addition to the first out-of-phase bending mode. Meters driven to oscillate in a different mode than the first out-of-phase bending mode experience the same phenomenon of multiple excited modes in addition to the intended drive mode.

Existing drive systems process a feedback signal, typically one of the pick-off sensor signals, to produce the drive signal. Unfortunately, the drive feedback signal contains responses from other modes in addition to the desired mode of excitation. Thus, the drive feedback signal is filtered through a frequency domain filter to remove unwanted components and the filtered signal is then amplified and applied to the driver. However, the frequency domain filter used to filter the drive feedback signal is not effective at isolating the single desired drive mode from other mode responses present in the drive feedback signal. There can be off-resonance responses from other modes which are near the desired mode resonance frequency. There might also be resonant responses at frequencies approaching the desired resonance frequency. In any event, the filtered drive feedback signal, i.e., the drive signal, typically contains modal content at frequencies other than just the desired mode for excitation of the flow tube. A drive signal composed of resonant response from multiple modes inputs, through the driver, energy to the flow tube that excites each mode for which the drive signal contains modal content. Such a multi-mode drive signal causes operational problems in Coriolis flowmeters. Further, frequency domain filters introduce phase lag in the filtered drive signal. This can result in a requirement for higher drive power to drive the flow tube at the desired amplitude.

One problem caused by a multi-mode drive signal is that external vibrations such as pipeline vibrations are reinforced by the drive signal. If pipeline vibrations external to the Coriolis flowmeter cause the flowmeter to vibrate, the drive feedback signal contains the response to the pipeline vibration. The frequency domain filter fails to remove the undesired response if the pipeline vibration falls at least in part within the frequency pass band of the filter. The filtered drive feedback signal, including the undesired response to the pipeline vibration, is amplified and applied to the driver. The driver then operates to reinforce the excitation mode of the pipeline vibration.

Another exemplary problem caused by a multi-mode drive signal occurs when the total amount of drive power available for driving the flow tubes is an issue. In order to meet intrinsic safety requirements set by various approvals agencies, the total power available at the driver of a Coriolis flowmeter is limited. This power limitation can be a problem for Coriolis flowmeters particularly with respect to larger flowmeters and more particularly with respect to larger flowmeters measuring fluids with entrained gas. A multi-mode drive signal is inefficient since it is putting energy into modes in addition to the desired drive mode. Thus the intrinsic safety power limitation is reached sooner than necessary for a given set of operating conditions.

A further problem is that, in the example of a meter driven at the first out-of phase bend mode, the driver location is also a position of maximum amplitude for the second out-of-phase bend mode. Hence the second out-of-phase bend mode is solidly excited in a Coriolis meter driven to oscillate at the first out-of-phase bend mode. The drive feedback signal, and subsequently the drive signal, therefore contains a response in the second out-of-phase bend mode.

An additional problem of a drive signal having modal content at multiple frequencies occurs with respect to the density measurement made by a Coriolis mass flowmeter. The density measurement in a Coriolis flowmeter or vibrating tube densitometer relies on the measurement of the resonant frequency of the vibrating flow tube. A problem arises when the flow tube is driven in response to a drive signal containing modal content at multiple modes. The superposition of the multiple modes in the drive signal can result in a flow tube that is driven off-resonance from the true resonant frequency of the desired drive mode. An error in the density measurement can result.

There is a need for a drive circuit system for a Coriolis flowmeter that drives the vibrating tube(s) of the flowmeter solely at the desired drive frequency. There exists a further need for a drive circuit system that enhances the desired drive mode in a drive feedback signal and suppresses unwanted vibration modes to produce a drive signal having modal content only at the desired drive frequency.

STATEMENT OF THE SOLUTION

The above identified problems, and others, are solved and a technical advance achieved in the field by the drive circuit system of the present invention. The present invention provides a method and apparatus for using a modal filter to generate a Coriolis flowmeter or densitometer drive signal. The modal filter receives feedback signals from the vibrating flow tube and produces a drive signal in which undesirable vibration modes are suppressed and desirable modes are enhanced. Thus, using the drive system of the present invention, a drive signal is produced that contains only the desired excitation mode of the Coriolis flowmeter flow tube(s).

The system of the present invention filters feedback signals from the flow tube of a Coriolis flowmeter through a modal filter. A modal filter is a spatial filter that utilizes a summation of multiple feedback signals measured at different points in space and/or in different directions in space, possibly including translational measurements and/or rotational measurements of motion, strain, force (or a combination of these) or other quantities related to flowmeter tube motion. The modal filter utilizes a summation of multiple feedback signals from different points along the length of a vibrating flow tube. The modal filter linearly combines weighted feedback signals to produce a resultant, filtered signal in which undesirable vibration modes are suppressed and desirable modes are enhanced. A feedback signal is representative of the motion of a flow tube, or the relative motion of multiple flow tubes, at a particular location on the flow tube(s). Typical Coriolis flowmeters already have available two feedback signals in the form of the signals from the pick-off sensors that are used in the mass flow rate computation of a Coriolis flowmeter. The signals generated by the pick-off sensors on a Coriolis flowmeter are utilized by the system of the present invention as feedback signals. A modal filter requires at least two feedback signals as input.

The drive system of the present invention is utilized in one embodiment to drive a Coriolis flowmeter having dual, parallel flow tubes. Two pick-off sensors provide two feedback signals. A third feedback signal is supplied by a sensor located at the position of the driver. The three feedback signals are fed into a modal filter. The modal filter includes an amplifier for each feedback signal. A different weighting factor, i.e. amplifier gain, is applied to each feedback signal and the three feedback signals are linearly combined by a summer in the modal filter. The resultant signal output from the modal filter is amplified to produce the drive signal and the drive signal is applied to the driver. The amplifier gains of the modal filter amplifiers are selected such that the modal filter operates to suppress modal content in the drive signal at the first out-of-phase twist mode and the second out-of-phase bending mode. Further, the drive signal has modal content substantially only at the first out-of-phase bending mode which is the desired drive mode of the flowmeter. The above-described signal processing could, of course, be implemented in discrete analog components or in a digital implementation. The terms "amplifier" and "summer" used herein, for example, apply to both analog and digital implementations.

The modal filter itself is comprised of a separate amplifier associated with each feedback signal and a summer for summing the weighted feedback signals. The magnitude of the gain of an amplifier in the modal filter is referred to as a weighting factor. The feedback signal is referred to as a weighted feedback signal after it has been amplified by its respective amplifier in the modal filter. The summer simply adds the weighted feedback signal to produce the filter output signal. The filter output signal does not have a large enough amplitude to drive the flow tubes and so the filter output signal is amplified to produce the drive signal. The drive signal has the same modal content but a greater amplitude than the filter output signal.

There are a number of ways to determine the weighting factors applied by the modal filter to the feedback signals. All of these various approaches are equivalent in their results but certain approaches are more efficient and repeatable than others. One approach is simply to select the weighting factors through trial and error until a drive signal is obtained having modal content substantially only at the desired drive mode. Various other approaches include calculating the inverse or pseudo-inverse of the matrix of eigenvectors of the flowmeter structure. Each row of this matrix comprises the appropriate weighting factors for a particular mode. The eigenvectors (or modal vectors) necessary to build the eigenvector matrix can be obtained through different means including, but not limited to, numerical means such as a finite element model of the flowmeter or experimental means such as experimental modal analysis. Another approach for determining the modal filter weighting factors is to use a technique known as the modified reciprocal modal vector method. A further approach is known as an adaptive modal filter. The means by which the weighting factors are determined is not critical and any one method or combination of methods is suitable.

The modal filter can be configured to filter a greater number of undesirable modes from the drive signal by using a greater number of feedback signals. At least two feedback signals must be supplied to the modal filter in order to achieve the beneficial effects of the present invention. For example, the two pick-off signals of a Coriolis flowmeter could be used as the sole feedback signals to the modal filter to produce a drive signal having two modes affected by the modal filter. In this case, the filter would effectively enhance the first out-phase-bending mode, i.e., the desired drive mode, and suppress the first out-of-phase twist mode. To totally suppress all undesired modes in a frequency range of interest requires as many feedback signals as the total number of modes in the frequency range of interest. If fewer feedback signals are available than number of modes, the amplitude of the desired mode is still enhanced relative to the amplitudes of the undesired modes, however, the response of the undesired modes cannot be totally eliminated.

The Coriolis flowmeter drive circuit modal filter of the present invention can be used to augment existing drive signal systems or it can be used in place of existing drive signal systems.

DETAILED DESCRIPTION

Figure 1:
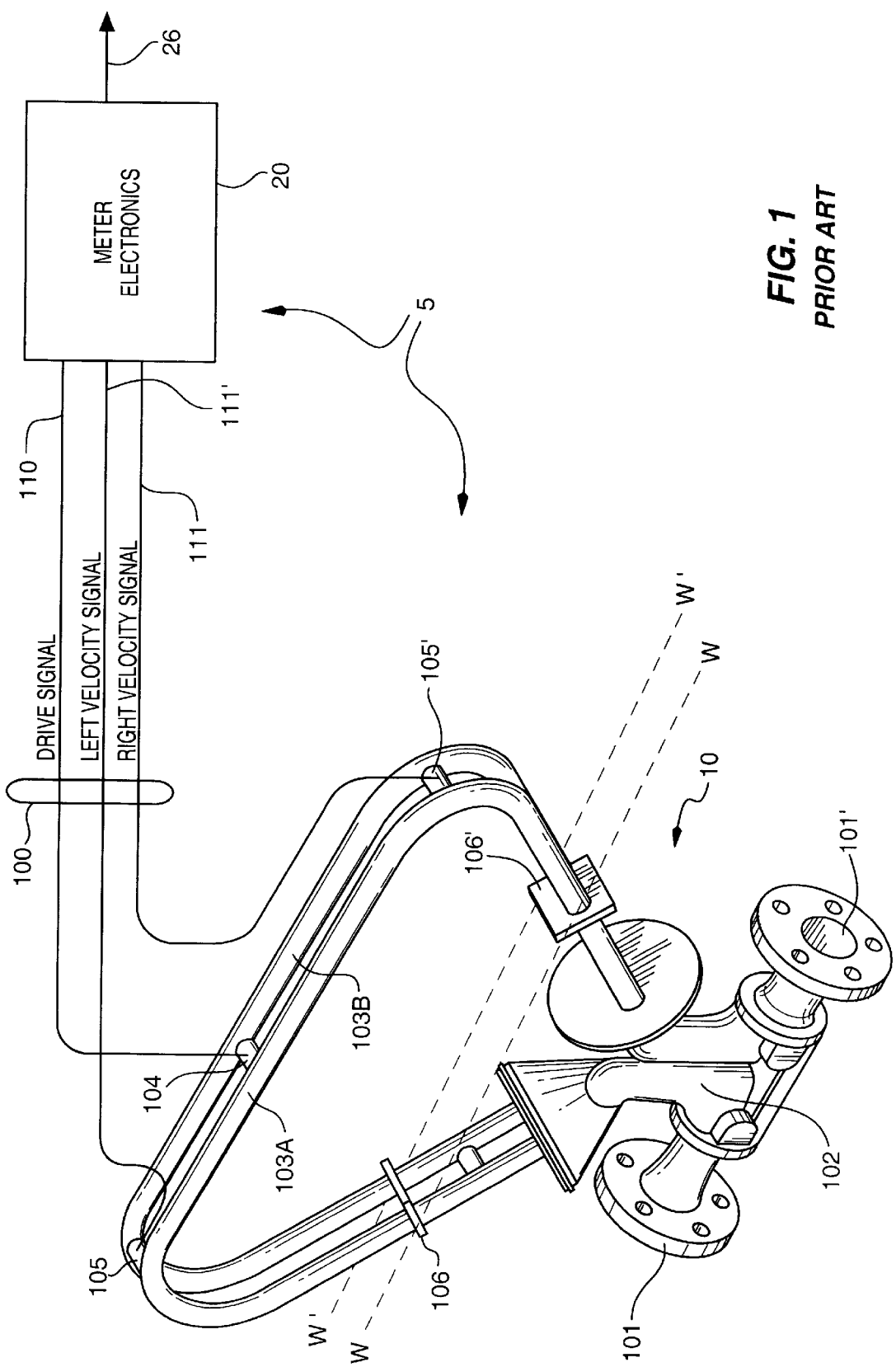
FIG. 1 depicts a Coriolis flowmeter and associated meter electronics.

Coriolis Flowmeter in General—FIG. 1

FIG. 1 shows a Coriolis flowmeter 5 comprising a Coriolis meter assembly 10 and meter electronics 20. Meter electronics 20 is connected to meter assembly 10 via leads 100 to provide density, mass flow rate, volume flow rate and totalized mass flow information over path 26. A Coriolis flowmeter structure is described although it is apparent to those skilled in the art that the present invention could be practiced in conjunction with a vibrating tube densitometer without the additional measurement capability provided by a Coriolis mass flowmeter.

Meter assembly 10 includes a pair of flanges 101 and 101', manifold 102 and flow tubes 103A and 103B. Connected to flow tubes 103A and 103B are driver 104 and pick-off sensors 105 and 105'. Brace bars 106 and 106' serve to define the axis W and W' about which each flow tube oscillates.

When flowmeter 10 is inserted into a pipeline system (not shown) which carries the process material that is being measured, material enters meter assembly 10 through flange 101, passes through manifold 102 where the material is directed to enter flow tubes 103A and 103B, flows through flow tubes 103A and 103B and back into manifold 102 from where it exits meter assembly 10 through flange 101'.

Flow tubes 103A and 103B are selected and appropriately mounted to the manifold 102 so as to have substantially the same mass distribution, moments of inertia and elastic modules about bending axes W—W and W'—W', respectively. The flow tubes extend outwardly from the manifold in an essentially parallel fashion.

Flow tubes 103A–103B are driven by driver 104 in opposite directions about their respective bending axes W and W' and at what is termed the first out of phase bending mode of the flowmeter. Driver 104 may comprise any one of many well known arrangements, such as a magnet mounted to flow tube 103A and an opposing coil mounted to flow tube 103B and through which an alternating current is passed for vibrating both flow tubes. A suitable drive signal is applied by meter electronics 20, via lead 110, to driver 104.

Meter electronics 20 receives the left and right velocity signals appearing on leads 111 and 111', respectively. Meter electronics 20 produces the drive signal appearing on lead 110 and causing driver 104 to vibrate tubes 103A and 103B. Meter electronics 20 processes the left and right velocity signals to compute the mass flow rate and the density of the material passing through meter assembly 10. This information is applied by meter electronics 20 over path 26 to a utilization means (not shown).

It is known to those skilled in the art that Coriolis flowmeter 5 is quite similar in structure to a vibrating tube densitometer. Vibrating tube densitometers also utilize a vibrating tube through which fluid flows or, in the case of a sample-type densitometer, within which fluid is held. Vibrating tube densitometers also employ a drive system for exciting the flow tube to vibrate. Vibrating tube densitometers typically utilize only single feedback signal since a density measurement requires only the measurement of frequency and a phase measurement is not necessary. The descriptions of the present invention herein apply equally to vibrating tube densitometers. Those skilled in the art recognize that where an existing Coriolis flowmeter already has two feedback signals available to input to a modal filter, an existing vibrating tube densitometer has only one feedback signal typically available. Thus one need only provide additional feedback signals in a vibrating tube densitometer in order to apply the present invention to a vibrating tube densitometer.

Figure 2:
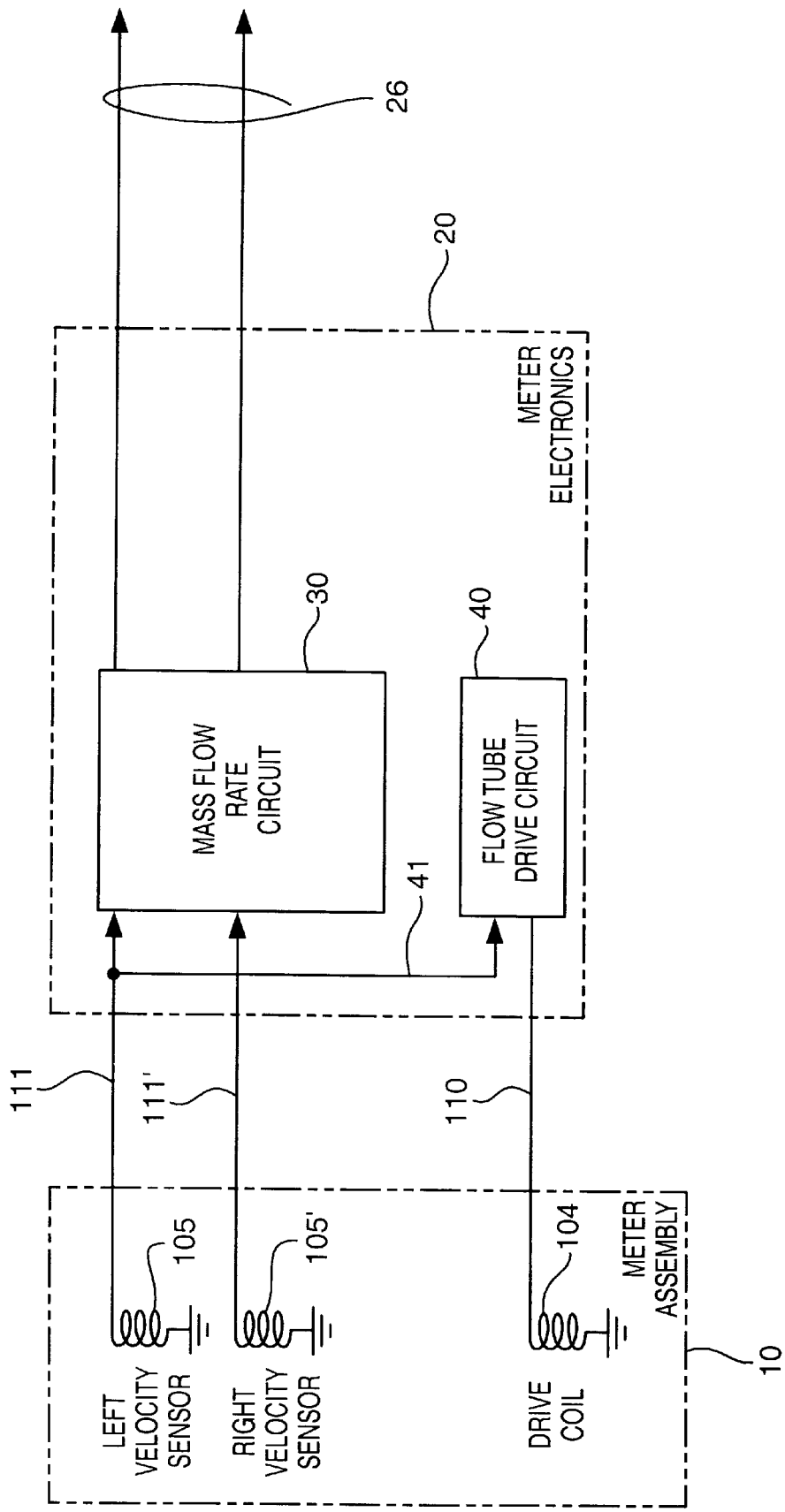
FIG. 2 depicts a block diagram of a prior art Coriolis flowmeter electronics.
Figure 3:
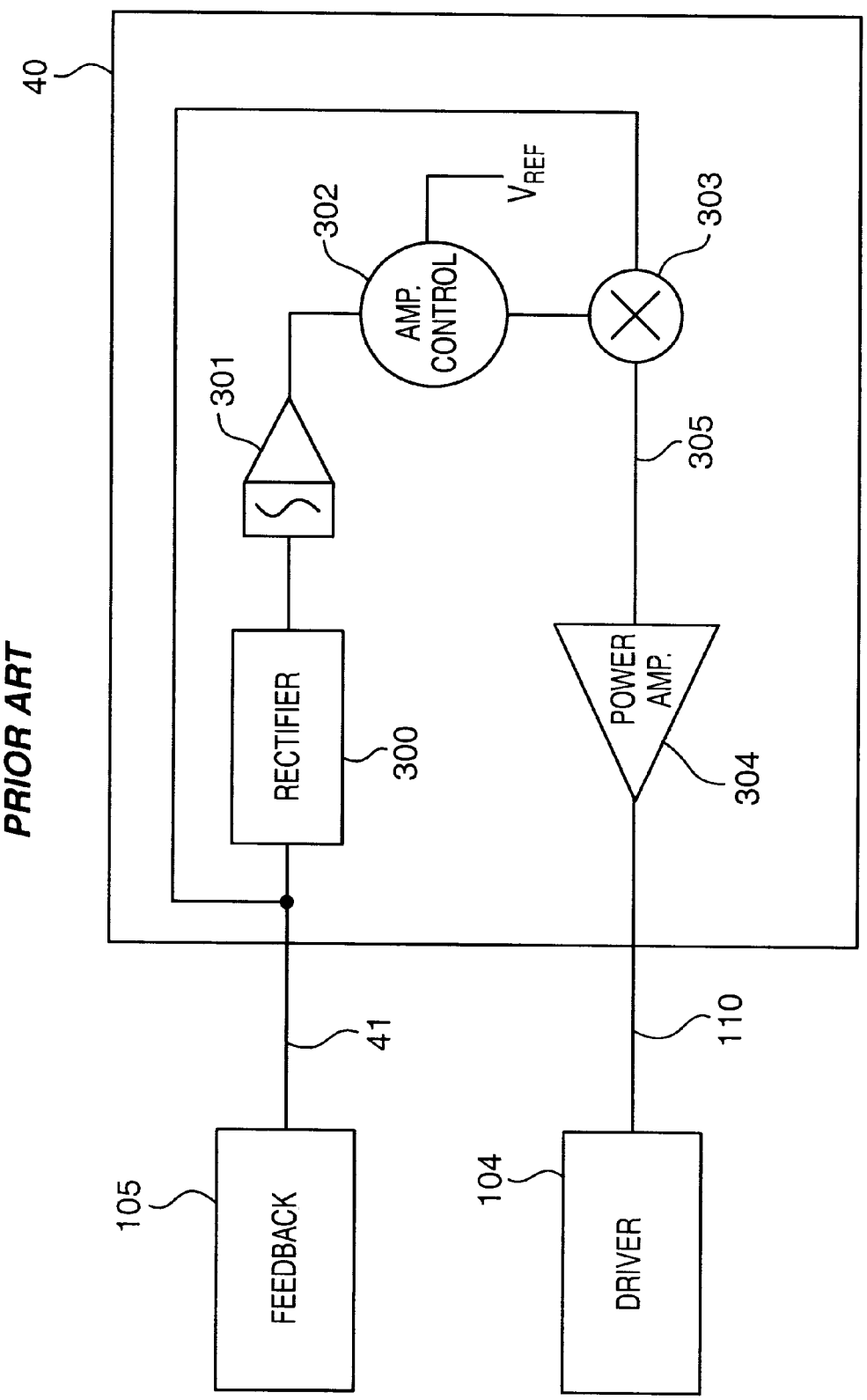
FIG. 3 depicts a block diagram of a prior art drive system for a Coriolis flowmeter.
Figure 6:
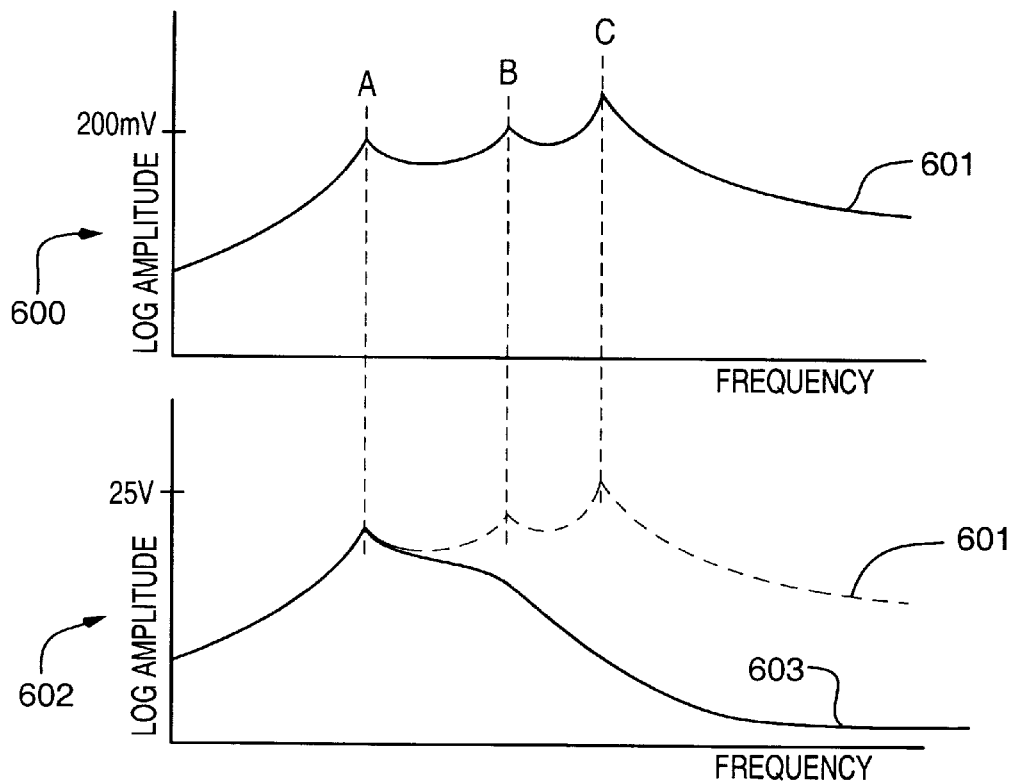
FIG. 6 depicts a frequency response function of a representative flow tube feedback signal and the frequency response function of the resultant drive signal according to an existing drive circuit.

Prior Art Drive System—FIGS. 2, 3 and 6

FIG. 2 depicts a block diagram of meter electronics 20. Meter electronics 20 includes mass flow rate circuit 30, and drive circuit 40. Mass flow rate circuit 30 is one of many known circuits for calculating the mass flow rate of a fluid through a vibrating tube based on the difference in phase between two points on the vibrating tube. Mass flow circuit 30 produces output to a utilization means (not shown) over line 26. The utilization means might be, for example, a display. The details of mass flow rate circuit 30 are well known to those skilled in the art and do not form part of the present invention. See U.S. Pat. RE 31,450 issued to Smith on Nov. 29, 1983 and assigned on its face to Micro Motion, Inc. or U.S. Pat. No. 4,879,911 issued to Zolock on Nov. 14, 1989 and assigned on its face to Micro Motion, Inc. or U.S. Pat. No. 5,231,884 issued to Zolock on Aug. 3, 1993 and assigned on its face to Micro Motion, Inc. for exemplary information regarding mass flow rate circuit 30.

In existing drive circuit systems, drive circuit 40 receives a feedback signal over path 41 from left pick-off sensor 105. As described in more detail with respect to FIG. 3, existing drive circuit systems produce a drive signal over path 110 to driver 104. Those skilled in the art recognize that existing drive systems may alternatively utilize the right pick-off sensor as the feedback to drive circuit 40. Also, some existing drive systems utilize the sum of both pick-off signals as the feedback to drive circuit 40.

FIG. 3 illustrates a block diagram of an existing drive circuit 40. Drive circuit 40 receives a feedback signal in the form of one of the pick-off signals from the flowmeter and appropriately conditions the magnitude of the pick-off signal to produce a drive signal over path 110. As noted, some existing drive systems sum the two pick-off signals and process the summed signal to produce a drive signal. Drive circuit 40 receives a signal from pick-off 105 over path 41. The pick-off signal is fed to rectifier 300 and then integrator 301. The signal output from integrator 301 represents an average amplitude of pick-off signal 105. The average amplitude signal is input to amplitude control 302. Amplitude control 302 compares the average amplitude signal from integrator 301 to a reference voltage $V_{ref}$. If the average amplitude falls below the reference voltage then the pick-off signal is amplified at multiplier 303 and an amplitude-conditioned pick-off signal is output from multiplier 303. The amplitude conditioned pick-off signal is amplified by power amplifier 304 to produce the final drive signal that is fed back to driver 104. Thus drive circuit 40 operates to maintain a relatively constant amplitude. The details of existing drive control circuitry 40 are well known to those skilled in the art of Coriolis flowmeter electronics and do not form part of the present invention. See U.S. Pat. No. 5,009,109 for a more detailed discussion of multiple embodiments of drive circuit 40.

FIG. 6 illustrates the modal content of the input to and output from drive circuit 40. FIG. 6 depicts two Frequency Response Function ("FRF") graphs 600 and 602 having vertical axes representing the log ratio of the flow tube response amplitude over the input force amplitude and horizontal axes representing frequency. The input force amplitude includes components due to the drive signal, fluid flow turbulence, external vibration sources, etc. It is assumed, for purposes of describing FIG. 6, that the input force has equal amplitude at all frequencies. The scales of the vertical axes of graphs 600 and 602 are different and the scales of the horizontal axes are the same. Graph 600 depicts a FRF 601 corresponding to a feedback signal. With reference to FIG. 3, FRF 601 characterizes a signal carried over path 41 from pick-off sensor 105 to existing drive circuit 40, with respect to the input force applied to the flow tube. FRF 601 has modal content at the first out-of-phase bend mode (amplitude peak at point A), first out-of-phase twist mode (amplitude peak at point B) and second out-of-phase bend mode (amplitude peak at point C). Graph 602 depicts a FRF 603 corresponding to a drive signal that is produced in an existing drive circuit using a frequency domain filter.

With reference to FIG. 3, FRF 603 characterizes a signal carried over path 110 from existing drive circuit 40 to driver 104, with respect to the input force applied to the flow tube. FRF 603 illustrates the effect of the frequency domain filtering of drive feedback signal 601. FRF 603 still has modal content from the same three modes that comprise signal 601 (indicated as a dotted line in graph 602) but the high frequency components drop off due to the frequency domain filtering of existing drive circuit 40.

Figure 4:
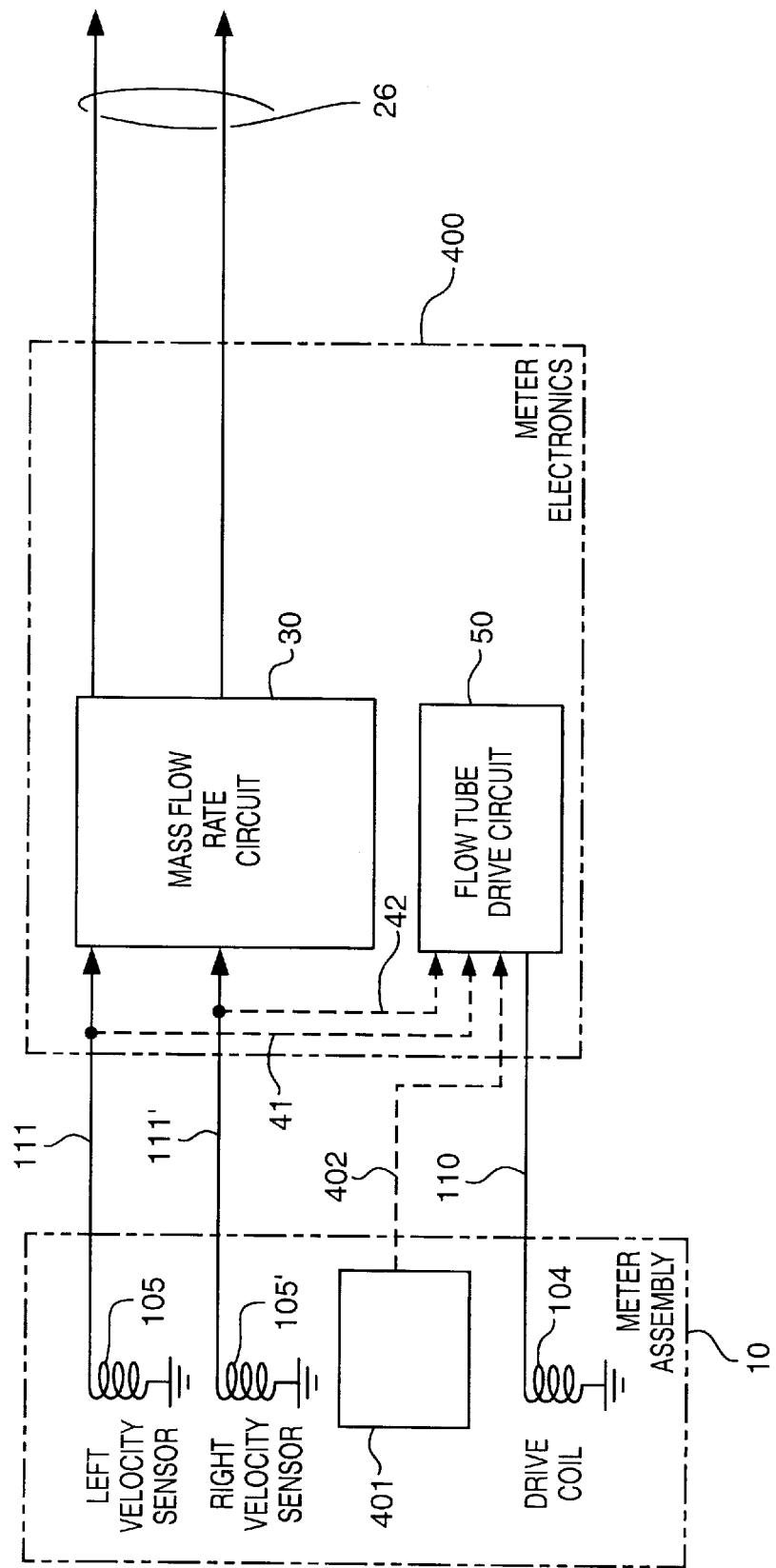
FIG. 4 depicts a block diagram of a Coriolis flowmeter electronics according to the present invention.
Figure 5:
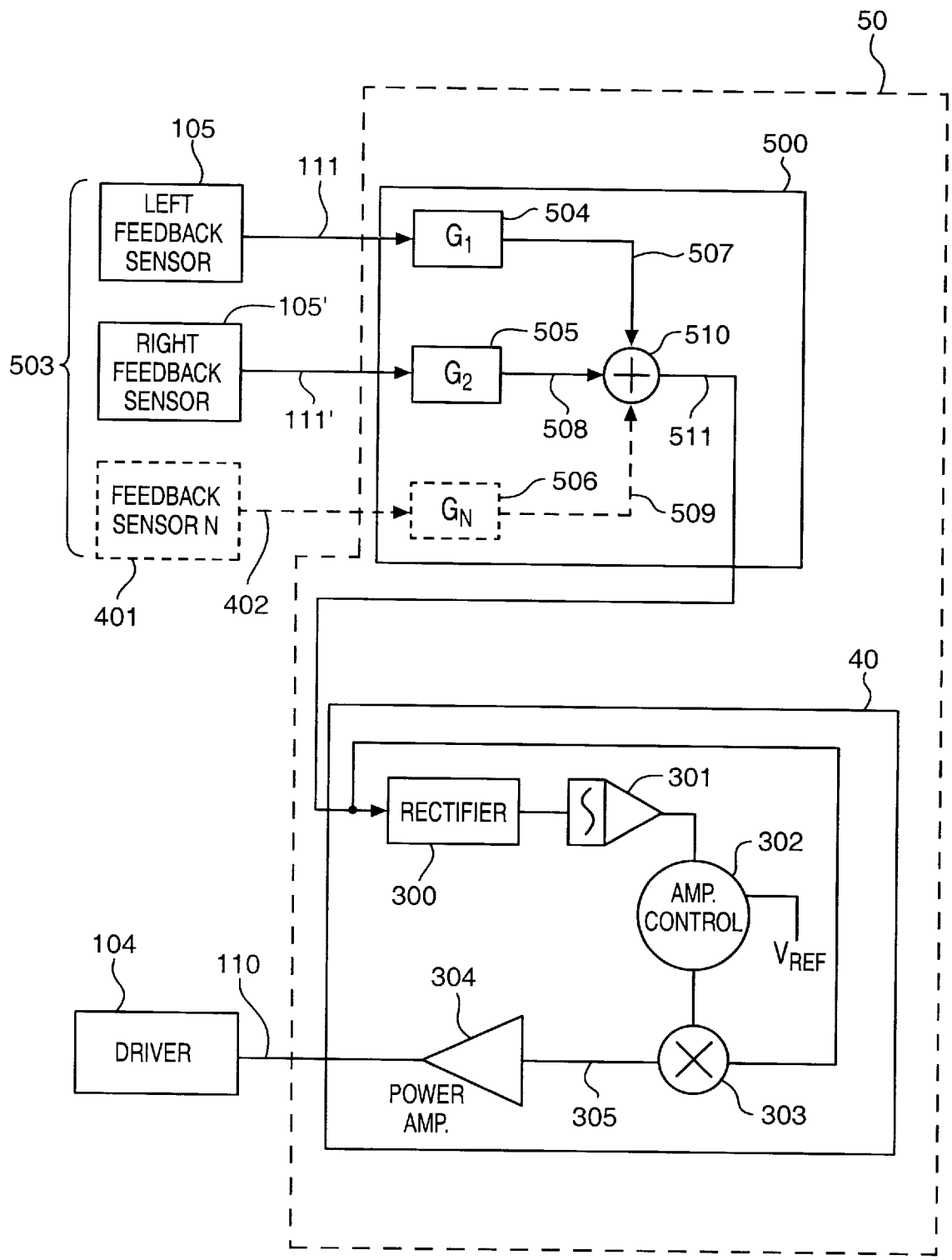
FIG. 5 depicts a block diagram of a Coriolis flowmeter drive system according to the present invention.
Figure 7:
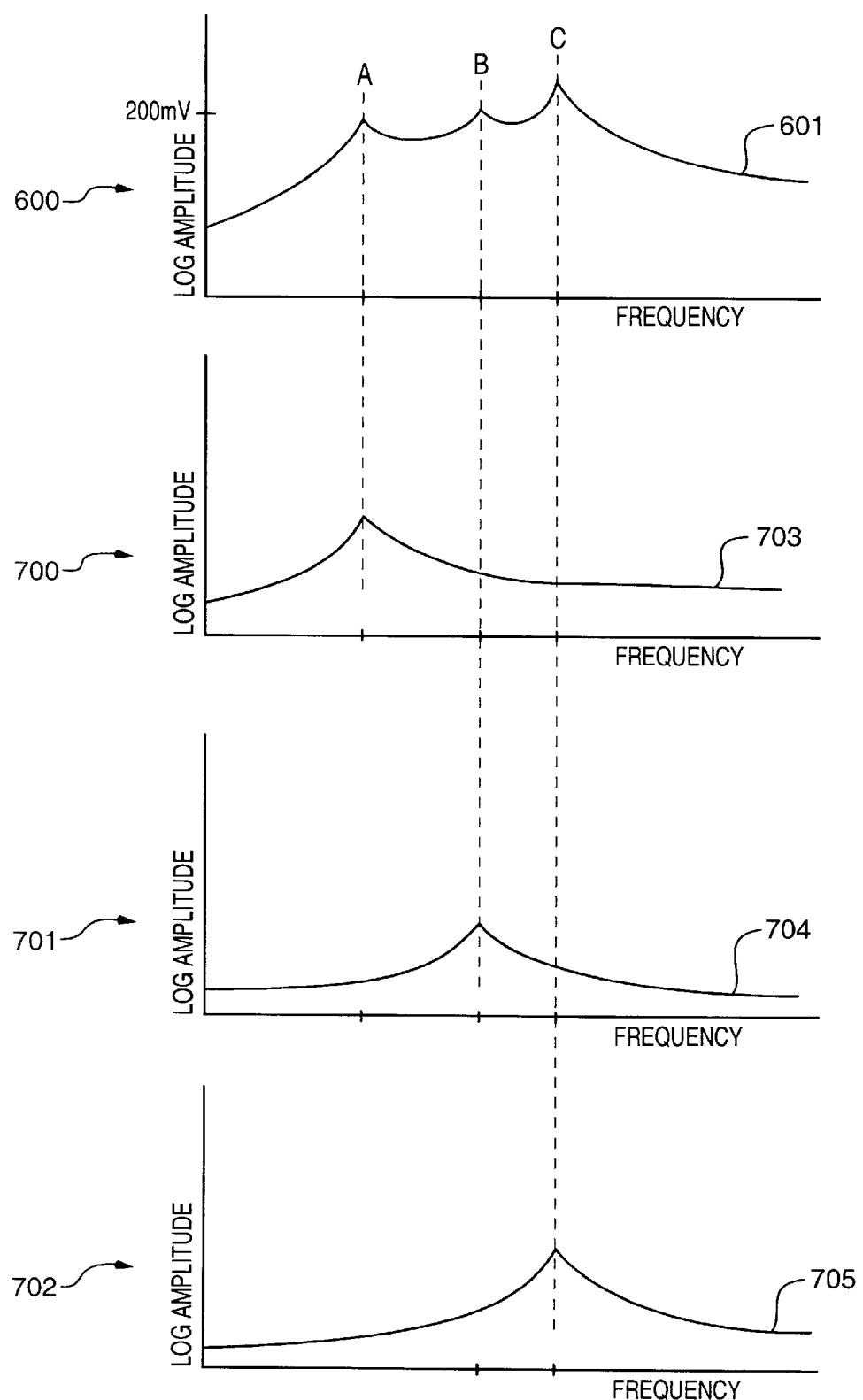
FIG. 7 depicts a frequency response function of a representative flow tube feedback signal and additional frequency response functions representing the contribution of constituent vibration modes to the feedback signal.

Drive System According to Present Invention—In General—FIGS. 4, 5 and 7

FIG. 4 depicts a block diagram of a meter electronics 400 including mass flow rate circuit 30 and flow tube drive circuit 50. Meter electronics 400 is similar to meter electronics 20, described with respect to FIGS. 2–3, with the following exceptions. Drive circuit 50 differs from drive circuit 40, as described in more detail with respect to FIG. 5. Also, drive circuit 50 receives additional feedback signals as inputs as compared to drive circuit 40. Left and right pick-off signals are received at drive circuit 50 over paths 41–42, respectively. Additional feedback signals are received from additional feedback sensor 401 over path 403. Feedback sensor 401 represents any number of additional feedback sensors attached to the flow tube(s) of a Coriolis flowmeter. In one embodiment of the present invention, discussed below, feedback sensor 401 is a pick-off sensor located at the position of the driver on the flow tube(s) of a Coriolis flowmeter.

FIG. 5 depicts a block diagram of drive circuit 50 including existing drive control circuit 40 and modal filter 500. Existing drive control circuit 40 is the same circuit described with respect to FIG. 3. Instead of receiving a pick-off signal directly from one of the pick-off sensors (feedback sensors 503), existing drive control circuitry 40 receives the signal output by modal filter 500. Modal filter 500 receives feedback signals from pick-off sensors 105–105' over paths 111–111', respectively. Sensor 401 represents any number of additional feedback sensors attached to the vibrating flow tube and producing a feedback signal to drive circuit 50. Each additional feedback signal produced by each additional feedback sensor is communicated to drive circuit 50 over a separate path 402. Pick-offs 105–105' and additional sensor (s) 401 are referred to herein collectively as feedback sensors 503. One skilled in the art recognizes that pick-offs 105–105' do not have to be used as one of feedback sensors 503. Preferably they are used, however, since they provide useful feedback signals, as described below, for purposes of modal filter 500 and they are necessary anyway for computation of mass flow rate.

Each of feedback signals 503 is input to one of amplifiers 504–506. Again, amplifier 506 represents any number of additional amplifiers for receiving signals from any number of additional feedback sensors 401. Amplifier 504 has a gain of $G_1$, amplifier 505 has a gain of $G_2$ and amplifier 506 has a gain $G_N$. Gains $G_1$–$G_N$ are referred to as the weighting factors applied by modal filter 500 to the feedback signals. The outputs of amplifiers 504–506 over paths 507–509 are referred to as the weighted feedback signals. The weighted feedback signals are summed by summer 510 to produce a filter output signal over path 511.

Gains $G_1$–$G_N$ of amplifiers 504–506 are selected such that the filter output signal over path 511 has an improved modal content as compared with any one of the feedback signals from feedback sensors 503. A filter output signal having improved modal content means a filter output signal in which a desired modal response is amplified and at least one undesired modal response is suppressed.

FIG. 7 illustrates the result of the modal filter described with respect to FIGS. 4–5. FIG. 7 includes, for comparison purposes, graph 600 from FIG. 6. Like graph 600, graphs 700–702 have vertical axes representing the log ratio of flow tube response amplitude over input force amplitude. Graphs 700–702 individually illustrate FRF's corresponding to the three modes of vibration which, when added through superposition, make up FRF 601. Graph 700 illustrates FRF 703 which corresponds to the first out-of-phase bend mode component of FRF 601. Graph 701 illustrates FRF 704 which corresponds to the first out-of-phase twist mode component of FRF 601. Graph 702 illustrates signal component 705 which corresponds to the second out-of-phase bend mode component of FRF 601. With reference to FIG. 5, FRF 601 characterizes a signal from one of feedback sensors 503 to modal filter 500. Modal filter 500 operates, as described above with respect to FIGS. 4–5, to remove all but the desired vibration mode from FRF 601. Thus, FRF 703, corresponding to the first out-of-phase bend mode component of FRF 601, represents the modal content of a signal over path 511 from modal filter 500 to drive control circuit 40. The actual drive signal over path 110 to driver 104 has a different amplitude than FRF 703 but the modal content of FRF 703 is unchanged by a simple amplification. Therefore the drive signal over path 110 to driver 104 from drive circuit 50 excites only the first out-of-phase bend mode of flow sensor 10. The difference between the drive signal produced by existing drive circuits and the drive signal produced by the drive circuit of the present invention is illustrated graphically by comparing FRF 603 of FIG. 6 (modal content of drive signal from existing drive circuit) and FRF 703 of FIG. 7 (modal content of drive signal from drive circuit of present invention).

Figure 8:
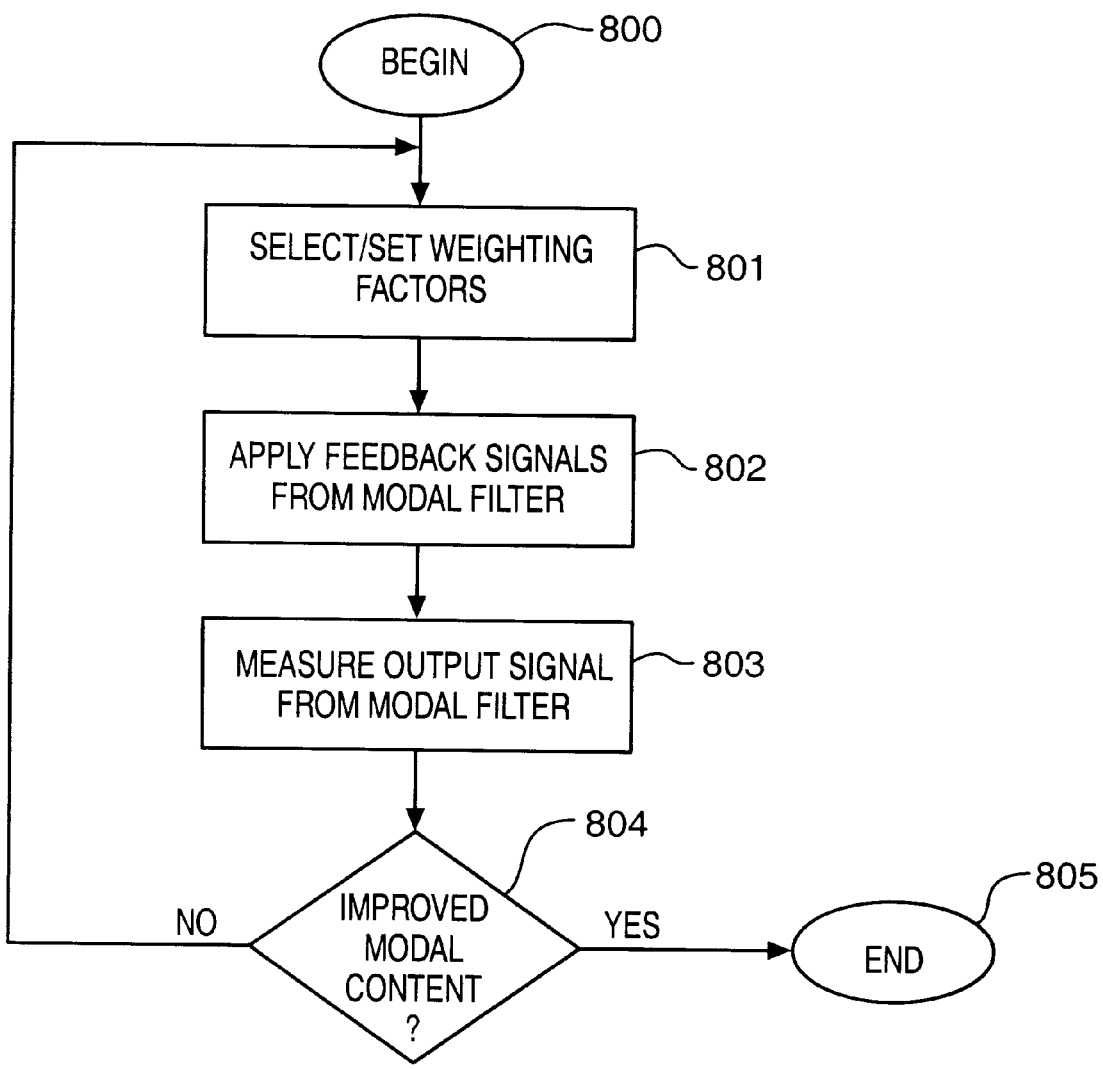
FIG. 8 is a flowchart illustrating the process steps for selecting modal filter weighting coefficients by trial and error.
Figure 9:
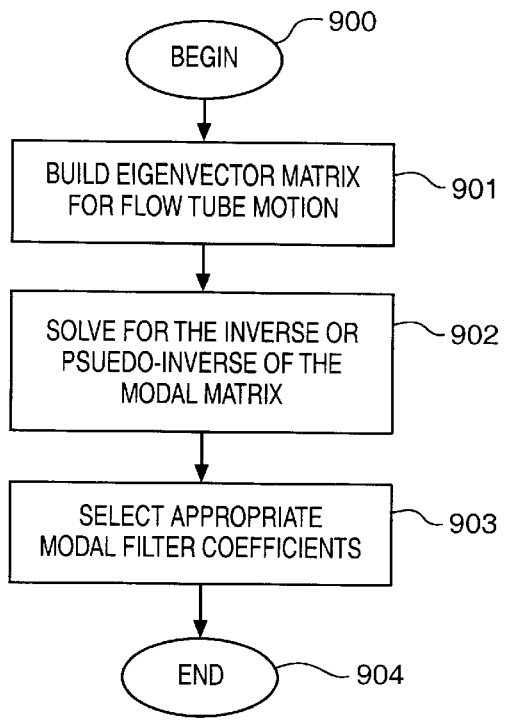
FIG. 9 is a flowchart illustrating the process for selecting modal filter weighting coefficients by calculating the inverse or pseudo-inverse of the eigenvector matrix.

Selection of Modal Filter Weighting Factors—FIGS. 8–9

Selection of weighting factors (gains $G_1$–$G_N$ in FIG. 5) for a Coriolis flowmeter drive circuit modal filter is discussed in more detail below with respect to FIGS. 8–9. There are a variety of methods one can use to select the weighting factors for the modal filter(s) applied to a drive circuit of a Coriolis mass flowmeter. The means by which the weighting factors are determined is not critical and any one method or combination of methods is suitable and equivalent.

One method of selecting the weighting factors for the modal filter(s) of a Coriolis drive circuit is trial and error. As noted with respect to FIGS. 5 and 7, the desired result of modal filter 500 is to produce a filter output signal having improved modal content as compared with any one of the feedback signals input to the modal filter. FIG. 8 is a flow chart illustrating the steps one uses to select modal filter weighting coefficients using a trial and error approach. Steps 801–804 are repeated until a filter output signal (drive signal) is obtained having the desired modal content. Steps 801–804 are conducted using an actual Coriolis flowmeter, properly instrumented to provide the necessary feedback signals along with a drive circuit that allows the changing of the gains of the modal filter amplifiers. Alternatively, the feedback signals can be recorded, for example in a Digital Audio Tape format, and re-applied to the modal filter drive circuit with each pass through steps 801–804. Alternatively, steps 801–804 are executed using a numerical model of a Coriolis flowmeter and associated drive circuit.

The process begins with step 800 and continues to step 801 where a first set of weighting coefficients are selected. During step 801, one can select a complete new set of weighting coefficients (gains $G_1$–$G_N$) each time step 801 is executed or one can select a new weighting coefficient for just one feedback signal each time step 801 is executed. During step 802 the feedback signals are applied to the modal filter where each modal filter amplifier has the gain set as determined by step 801. During step 803 the filter output signal is measured and recorded as appropriate to allow the necessary comparison with the feedback signal input to the modal filter. Processing continues from step 803 to decision block 804.

Decision block 804 operates to determine if the filter output signal has improved modal content as compared to any one of the feedback signals input to the modal filter. The user determines what modal content in the filter output signal is satisfactory. Thus, "improved modal content" can mean a filter output signal in which only modal content from the desired drive mode is present. "Improved modal content" can also mean, depending on the user's specifications, that the desired drive mode amplitude is at least 20 dB greater than the amplitude of the other modes present, for example. If it is determined, by operation of decision block 804, that the filter output signal has improved modal content then processing continues to step 805 where the weighting coefficient process concludes. If it is determined that the filter output signal does not have improved modal content then processing returns to step 801. A new set of weighting coefficients is selected during step 801 and steps 802–804 are processed again to locate a set of weighting coefficients that produce a filter output signal having improved modal content.

A method of selecting the weighting coefficients for a Coriolis flowmeter drive circuit is to calculate the inverse or pseudo-inverse of the eigenvector matrix. As noted above, a vibrating flow tube of a Coriolis flowmeter has present a combination of vibration modes. Analyzing the flow tube motion in physical coordinates, e.g. the singular response at individual points and directions on the flow tube, requires the analysis of coupled equations which do not easily yield useful information about the motion of the flow tube. However, one can use a modal transformation to transform a vector of physical responses to the modal responses or modal coordinates of the system. The standard modal transformation is given by:

$$x = \phi \eta \qquad (1)$$

where:
  x is the vector of physical response coordinates
  $\phi$ is the eigenvector matrix, the columns of which are the flow tube eigenvectors (also referred to as modal vectors) of interest, and
  $\eta$ is the vector of modal response coordinates.

The eigenvector matrix can, as described below, be developed for any Coriolis flowmeter flow tube. The physical vectors can be thought of as the input, i.e. the feedback signals, to the modal filter. Therefore equation (1) is solved for $\eta$, the modal coordinate response(s) as follows:

$$\eta = \phi^+ x \qquad (2)$$

Putting equation (1) in the form of equation (2) requires taking the pseudo-inverse of the eigenvector matrix $\phi$. If the eigenvector matrix is square and non-singular then the inverse of the eigenvector matrix ($\phi^{-1}$) is used in Equation (2) rather than the pseudo-inverse. The eigenvector matrix is square and non-singular when the number of feedback signals from the flow tube equals the number of modes considered and the modal vectors are linearly independent.

The following example is utilized to illustrate the process by which one calculates the psuedo-inverse of a modal matrix to determine the weighting coefficients for a Coriolis flowmeter drive circuit modal filter. One could use a physical or a numerical model of the flowmeter to build the eigenvector matrix. In the following example a numerical model of the flowmeter was used.

A finite element model is built of the tubes of a CMF100 model Coriolis mass flowmeter (manufactured by Micro Motion, Inc.). The model fixes to ground the ends of the flow tubes that, on a physical flowmeter, connect to the flowmeter manifold. Finite element modeling techniques are well known to those skilled in the art and do not form part of the present invention. The exemplary finite element model was built using SDRC-Ideas and analyzed by MSC/NASTRAN, a finite element code available from MacNeal-Schwendier. Those skilled in the finite element modeling art recognize that any finite element code could alternatively be used. The locations of the feedback sensors were modeled to produce output representative of the relative motion between the locations on the flow tube of the magnet and coil corresponding to the right pick-off, the drive and the left pick-off. These "scalar points" are a standard technique in advanced dynamic analysis. See "A Finite Element for the Vibration Analysis of a Fluid-Conveying Timeshenko Beam.". (AIM Paper 93-1552), for more information on finite element modeling of Coriolis flowmeters.

The eigenvalue coefficients of the CMF100 model are extracted from the finite element model to build the following 3 row by 10 column eigenvector matrix for the CMF100 sensor:

$$\phi_{full} = \begin{pmatrix} 0 & 25.08 & 0 & 0 & 0 & -40.3 & 0 & 0 & 0 & 36.78 \\ 0 & 35.39 & 0 & 0 & 0 & 0 & 0 & 0 & 0 & -36.55 \\ 0 & 25.08 & 0 & 0 & 0 & 40.3 & 0 & 0 & 0 & 36.78 \end{pmatrix} \quad (3)$$

Each row in the full eigenvector matrix $\phi_{full}$ of equation (3) corresponds to a physical location on the flow tube. The first row corresponds to the left pick-off location, the second row corresponds to the driver location and the third row corresponds to the right pick-off location. Each column in the full eigenvector matrix $\phi_{full}$ corresponds to a mode of vibration. This matrix is used in a known fashion by the finite element model to model the signals generated by the pick-off sensors. The matrix is used, as described below, to develop the weighting coefficients for the drive circuit modal filter. The columns (modes) with zeroes in the full eigenvector matrix $\phi_{full}$ are "in-phase modes". This means that there is no relative motion between the tubes because both tubes are moving with the same speed and direction. Thus, the sensors used to provide feedback signals, velocity sensors in this example, themselves act as a kind of modal filter by filtering out all the in-phase modes. The full eigenvector matrix $\phi_{full}$ is reduced by removing all the in-phase columns.

$$\phi_{reduced} = \begin{pmatrix} 25.1 & -40.3 & 36.8 \\ 35.4 & 0 & -36.6 \\ 25.1 & 40.3 & 36.8 \end{pmatrix} \quad (4)$$

Equation (4) is the reduced eigenvector matrix $\phi_{reduced}$. Equation (1), the standard modal transformation, is rewritten using the reduced eigenvector matrix $\phi_{reduced}$ as follows:

$$\begin{pmatrix} RPO \\ DRV \\ LPO \end{pmatrix} = \begin{pmatrix} 25.1 & -40.3 & 36.8 \\ 35.4 & 0 & -36.6 \\ 25.1 & 40.3 & 36.8 \end{pmatrix} \cdot \begin{pmatrix} n_b \\ n_t \\ n_{2b} \end{pmatrix} \quad (5)$$

where $\eta_b$ is the first out-of-phase bend mode modal coordinate response, $\eta_t$ is the first out-of-phase twist mode modal coordinate response and $\eta_{2b}$ is the second out-of-phase bend mode modal coordinate response and RPO is the physical response from the right pick-off sensor, DRV is the physical response from the feedback sensor at the drive location and LPO is the physical response from the left pick-off sensor. Equation (5) is solved for the unknown vector quantities, i.e., the modal vectors:

$$\begin{pmatrix} n_b \\ n_t \\ n_{2b} \end{pmatrix} = \begin{pmatrix} 25.1 & -40.3 & 36.8 \\ 35.4 & 0 & -36.6 \\ 25.1 & 40.3 & 36.8 \end{pmatrix}^{-1} \cdot \begin{pmatrix} RPO \\ DRV \\ LPO \end{pmatrix} \quad (6)$$

The reduced eigenvector matrix is inverted by importing the matrix into a standard, commercial mathematical computation package such as Mathcad and utilizing one of the standard inversion or pseudo-inversion functions available in these computing packages. The resulting equation is shown as equation (7):

$$\begin{pmatrix} n_b \\ n_t \\ n_{2b} \end{pmatrix} = \begin{pmatrix} 8.23892 \cdot 10^{-3} & 1.657905 \cdot 10^{-2} & 8.23892 \cdot 10^{-3} \\ -1.240777 \cdot 10^{-2} & 0 & 1.240777 \cdot 10^{-2} \\ 7.975764 \cdot 10^{-3} & 1.130755 \cdot 10^{-2} & 7.975763 \cdot 10^{-3} \end{pmatrix} \cdot \begin{pmatrix} RPO \\ DRV \\ LPO \end{pmatrix}$$

The numerical coefficients in Equation (7) are the weighting factors for the modal filter amplifiers in a Coriolis flowmeter drive circuit. For example, if one desires to extract the first out-of-phase bend mode from the feedback signals, as is the case here, then the first row of the above modal filter vector matrix is used as follows:

$$\eta_b = 8.2389(RPO) + 16.5795(DRV) + 8.2389(LPO) \quad (8)$$

The first out-of-phase bend mode modal vector coefficients were multiplied by $10^3$ to simplify Equation (8). With reference to FIG. 5, gain $G_1$ of amplifier 504 is set to 8.2389 (the modal filter vector coefficient corresponding to the left pick-off sensor), gain $G_2$ is set to 8.2389 (the modal filter vector coefficient corresponding to the right pick-off sensor) and gain $G_N$ is set to 16.5795 (the modal filter vector coefficient corresponding to the driver location). The weighting factors are linearly scaled as a group to provide a filter output signal over path 511 having the proper amplitude for input into drive control circuit 40.

FIG. 9 is a flowchart illustrating the process steps for determining the drive circuit modal filter coefficients by calculating the inverse or pseudo-inverse of the eigenvector matrix. Calculation of the inverse or pseudo-inverse of the eigenvector matrix described above and with respect to FIG. 9 is known to those skilled in the art of advanced dynamic analysis and is a useful tool for determining the drive circuit modal filter coefficients. The flowchart of FIG. 9 begins with element 900 and proceeds to step 901. During step 901 the eigenvector matrix is built. As noted above, a method of determining the eigenvectors for the eigenvector matrix is by building a finite element model of the flowmeter from which the eigenvectors are extracted. Another approach is to use experimental modal analysis to determine the eigenvectors directly from a physical sample of the flowmeter. Experimental modal analysis is well known to those skilled in the art and its methods and use do not form part of the present invention. Once the eigenvectors are obtained by any appropriate method, the eigenvector matrix is compiled. Equation (3) is an example of a full eigenvector matrix for 10 modes of vibration at three points on the flow tubes. Each column of the eigenvector matrix represents a different mode while the number of rows of the eigenvector matrix represents degrees of freedom. The eigenvector matrix is then reduced to the modes to be filtered. For the current example this is done by eliminating the columns with O's as coefficients. For the exemplary structure and sensors described herein, the columns (modes) with coefficients as O's are in-phase modes. Processing proceeds from step 901 to step 902.

During step 902 the inverse or pseudo-inverse of the eigenvector matrix is calculated. Each row of the inverse or pseudo-inverse of the eigenvector matrix contains the modal filter coefficients associated with a particular mode. This is expressed in general by Equation (2) and is shown for the above example by Equation (7). Processing next proceeds to step 903.

During step 903 the appropriate modal filter weighting coefficients are selected. In the above example the flowmeter is driven in the first out-of-phase bend mode and therefore the modal filter coefficients for the first out-of-phase bend mode are selected. However, one could build different modal filters for different applications by selecting the modal filter coefficients for different modes. For example, one might build a flowmeter having multiple drivers positioned to drive the flow tube in the first out-of-phase twist mode instead of the first out-of-phase bend mode. In this case the modal filter coefficients for the first out-of-phase twist mode, i.e. the second line in Equation (7), are used as the weighting coefficients for the modal filter. A further example is where one chooses to simultaneously and precisely excite multiple modes in a Coriolis flow tube. If one wants to drive a flow tube at both the first out-of-phase bend mode and the first out-of-phase twist mode then two modal filters are used. One modal filter uses the weighting coefficients for the first out-of-phase mode and produces a filter output signal having modal content only at the first out-of-phase bend mode. The second modal filter uses the weighting coefficients for the first out-of-phase twist mode and produces a filter output signal having modal content only at the first out-of-phase twist mode. The two filter output signals are summed to develop a drive signal having modal content only at the first out-of-phase bend mode and the first out-of-phase twist mode. After selecting the appropriate modal filter weighting coefficients, processing concludes with element 904.

Figure 10:
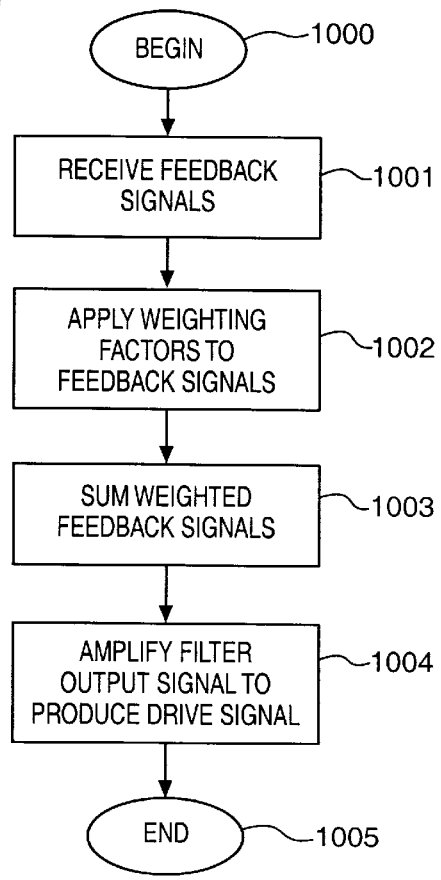
FIG. 10 is a flowchart illustrating the process for using a modal filter to develop a flowmeter drive signal.

Flowmeter Drive Circuit Modal Filter Flowchart—FIG. 10

FIG. 10 is flowchart illustrating the processing steps for utilizing a modal filter to produce a Coriolis flowmeter drive signal. Processing begins with step 1000 and proceeds to step 1001. During step 1001 the modal filter drive circuit receives two or more feedback signal signals from the vibrating flow tube. Processing next proceeds to step 1002 where each feedback signal is amplified by its corresponding weighting factor. The weighted feedback signals are, during step 1003, summed to produce a filter output signal. During step 1004, the filter output signal is amplified to produce a drive signal which is fed back to the flow tube drive element. Step 1004 may also include a gain control function. This process continues until element 1005 during which operation of the flowmeter concludes.

Although specific embodiments are disclosed herein, it is expected that persons skilled in the art can and will design alternative Coriolis flowmeter drive systems employing modal filters that are within the scope of the following claims either literally or under the Doctrine of Equivalents.

I claim:

1. A drive system for vibrating a fluid container, comprising:

drive means positioned adjacent said fluid container and responsive to a drive signal for vibrating said fluid container;

first sensor means attached to a first location on said fluid container for producing a first motion signal indicative of the movement of said fluid container at said first location;

second sensor means attached to a second location on said fluid container for producing a second motion signal indicative of the movement of said fluid container at said second location;

said first and second motion signals representing a plurality of vibration modes of said fluid container; and spatial filter means for receiving said first and second motion signals and generating said drive signal, said drive signal representing less vibration modes than said plurality of vibration modes.

2. The drive system of claim 1 wherein said fluid container is a flow tube through which fluid flows.

3. The drive system of claim 2 wherein said flow tube is part of a Coriolis mass flowmeter.

4. The drive system of claim 2 wherein said flow tube is part of a vibrating tube densitometer.

5. The drive system of claim 2 wherein said drive means is attached to said flow tube.

6. The drive system of claim 2 wherein said spatial filter means includes:

first weighting means for applying a first weighting factor to said first motion signal to develop a first weighted signal;

second weighting means for applying a second weighting factor to said second motion signal to develop a second weighted signal; and summing means for combining said first weighted signal and said second weighted signal to produce said drive signal.

7. The drive system of claim 6 wherein said summing means includes:

summing means for combining said first weighted signal and said second weighted signal to produce a modally filtered signal, which is a signal filtered of some of said plurality of vibration modes; and amplification means for amplifying said modally filtered signal to produce said drive signal.

8. The drive system of claim 7 further comprising:

a third sensor means attached to a third location on said flow tube for producing a third motion signal indicative of the movement of said flow tube at said third location.

9. The drive system of claim 8 wherein said third location is near a position at which said drive means interacts with said flow tube.

10. The drive system of claim 8 further comprising:

third weighting means for applying a third weighting factor to said third motion signal to develop a third weighted signal; and summing means for combining said first, second and third weighted signals to produce said drive signal.

11. The drive system of claim 6 wherein said first and second weighting means are analog amplifiers.

12. The drive system of claim 6 wherein said spatial filter means further includes:
an analog to digital converter for converting said first and second motion signals to digital signals; and
said first and second weighting means being digital amplifiers.

13. The drive system of claim 1 wherein said first and second sensor means are velocity sensors.

14. The drive system of claim 1 wherein said first and second sensor means are position sensors.

15. The drive system of claim 1 wherein said first and second sensor means are acceleration sensors.

16. The drive system of claim 1 wherein said first and second sensor means are strain gauges.

17. The drive system of claim 1 further including:
amplitude control means, responsive to said drive signal and a reference voltage, for maintaining a maximum vibration amplitude of said fluid container at a substantially constant level.

18. A method for vibrating a fluid container, comprising the steps of:
receiving a first motion signal indicative of the movement of said fluid container at a first location on said fluid container, said first motion signal representing a plurality of vibration modes of said fluid container;
receiving a second motion signal indicative of the movement of said fluid container at a second location on said fluid container, said second motion signal representing a plurality of vibration modes of said fluid container;
spatially filtering said first and second motion signals to generate a drive signal, said drive signal having less vibration modes than said plurality of vibration modes; and
applying said drive signal to a driver operative to cause said fluid container to vibrate in response to said drive signal.

19. The method of claim 18 wherein said applying step includes:
applying said drive signal to a driver operative to cause said fluid container to vibrate in response to said drive signal where said fluid container is a flow tube of a vibrating tube flowmeter.

20. The method of claim 18 wherein said spatially filtering step includes:
applying a first weighting factor to said first motion signal to develop a first weighted signal;
applying a second weighting factor to said second motion signal to develop a second weighted signal; and
summing said first weighted signal and said second weighted signal to produce said drive signal.

21. The method of claim 20 wherein said summing step includes:
summing said first weighted signal and said second weighted signal to produce a modally filtered signal; and
amplifying said modally filtered signal to produce said drive signal.

22. The method of claim 21 further comprising:
receiving a third motion signal indicative of the movement of said fluid container at a third location on said fluid container, said third motion signal having modal content at a plurality of vibration modes.

23. The method of claim 22 further comprising:
applying a third weighting factor to said third motion signal to develop a third weighted signal; and
summing said first, second and third weighted signals to produce said drive signal.

24. The method of claim 18 further comprising:
controlling a maximum vibration amplitude of said fluid container, responsive to said drive signal and a reference voltage, for maintaining said maximum vibration amplitude of said fluid container at a substantially constant level.

25. A method for generating modal filter weighting factors for a modal filter in a drive system for a measurement instrument employing a vibrating tube, comprising the steps of:
building an eigenvector matrix for the motion of said vibrating tube at N locations on said vibrating tube wherein N is an integer number greater than or equal to one;
solving for the inverse of the psuedo-inverse of the eigenvector matrix to obtain a modal filter vector for said vibrating tube, said modal filter vector containing N sets of coefficients wherein each one of said N sets of coefficients relates to one of a plurality of vibration modes present on said vibrating tube; and
selecting one of said N sets of coefficients as said modal filter weighting factors to be applied to feedback signals from feedback sensors located at said N locations on said vibrating tube.

26. The method of claim 25 wherein said building step includes:
performing an experimental modal analysis on said vibrating tube to generate eigenvectors for said eigenvector matrix.

27. The method of claim 25 wherein said building step includes;
developing a finite element model of said vibrating tube; and
extracting eigenvectors from said finite element model for said eigenvector matrix.

28. The method of claim 25 wherein said solving step includes:
solving the equation $x=\phi\eta$ for $\eta$ where:
x is a vector of physical response coordinates
$\phi$ is said eigenvector matrix, and
$\eta$ is said modal filter vector containing said N sets of coefficients.

29. The method of claim 28 wherein said selecting step includes:
determining which of said plurality of vibration modes present on said vibrating tube is to be extracted as a drive signal for causing said vibrating tube to vibrate; and
selecting, responsive to said determining step, a desired set of coefficients from said N sets of coefficients as said modal filter weighting factors.

30. A method for characterizing a modal filter in a drive system for a vibrating tube flowmeter, comprising the steps of:
choosing a temporary first weighting factor and a temporary second weighting factor;
receiving a first feedback signal from a first feedback sensor attached at a first location on a flow tube of said vibrating tube flowmeter,
receiving a second feedback signal from a second feedback sensor attached at a second location on said flow tube of said vibrating tube flowmeter;
applying said temporary first weighting factor to said first feedback signal to produce a first weighted signal;

applying said temporary second weighting factor to said second feedback signal to produce a second weighted signal;

summing said first and second weighted signals to produce a drive signal;

determining whether said drive signal has modal contents of desired modes as compared to said first and second feedback signals; and selecting said temporary first weighting factor as an operational first weighting factor and said temporary second weighting factor as an operational second weighting factor in response to determining that said drive signal has said modal content of said desired modes.

* * * * *

UNITED STATES PATENT AND TRADEMARK OFFICE
CERTIFICATE OF CORRECTION

PATENT NO.     : 6,199,022 B1
DATED          : March 6, 2001
INVENTOR(S)    : Timothy J. Cunningham Page 1 of 2

It is certified that error appears in the above-identified patent and that said Letters Patent is hereby corrected as shown below:

Column 11,
Line 19, replace "a finite element code available from MacNeal-Schwendier." with
-- a finite element code available from MacNeal-Schwendler. --
Line 28, replace "Analysis of a Fluid-Conveying Timeshenko Beam.". (AIM" with
-- Analysis of a Fluid-Conveying Timeshenko Beam.". (AIAA) --

Column 13,
Line 3, replace "in the art and its methods and use do not form part of the" with
-- in the art and its methods and use to not form part of the --

Column 14, claim 11,
Lines 64-65, replace "11. The drive system of claim 6 wherein said first and second weighting means are analog amplifiers." with -- 11. The drive system of claim 1 wherein said first and second sensor means are velocity sensors. --

Column 15, claim 12,
Lines 1-6, replace "12. The drive system of claim 6 wherein said spatial filter means further inclues: an analog to digital converter for converting said first and second motion signals to digital signals; and said first and second weighting means being digital amplifers." with -- 12. The drive system of claim 1 wherein said first and second sensor means are position sensors. --
Line 8, replace "second sensor means are velocity sensors." with -- second sensor means are acceleration sensors. --
Line 10, replace "second sensor means are position sensors." with -- second sensor means are strain gauges. --

Column 15, claim 15,
Lines 11-12, repalce "15. The drive system of claim 1 wherein said first and second sensor means are acceleration sensors." with --15. The drive system of claim 6 wherein said first and second weighting means are analog amplifiers. --

Column 15, claim 16,
Lines 13-14, replace "16. The drive system of claim 1 wherein said first and second sensor means are strain gauges." with -- 16. The drive system of claim 6 wherein said spatial filter means further includes: an analog to digital converter for converting said first and second motion signals to digital signals; and said first and second weighting means being digital amplifiers. --

UNITED STATES PATENT AND TRADEMARK OFFICE
CERTIFICATE OF CORRECTION

PATENT NO. : 6,199,022 B1
DATED : March 6, 2001
INVENTOR(S) : Timothy J. Cunningham It is certified that error appears in the above-identified patent and that said Letters Patent is hereby corrected as shown below:

<u>Column 16,</u>
Line 61, replace "vibrating tube flowmeter," with -- vibrating tube flowmeter; --

Signed and Sealed this

Eighteenth Day of December, 2001

Attest:

JAMES E. ROGAN
*Attesting Officer*     *Director of the United States Patent and Trademark Office*